US005672756A

United States Patent [19]

Shimada et al.

[11] Patent Number: 5,672,756

[45] Date of Patent: Sep. 30, 1997

[54] TRIPHENYLAMINE COMPOUND FOR USE IN ELECTROPHOTOGRAPHIC PHOTOCONDUCTORS

[75] Inventors: Tomoyuki Shimada, Shizuoka-ken; Masaomi Sasaki, Susono; Tamotsu Aruga, Mishima; Masafumi Ohta, Susono; Mitsutoshi Anzai; Akihiro Imai, both of Kawasaki, all of Japan

[73] Assignees: Ricoh Company, Ltd., Tokyo; Hodogaya Chemical Co., Ltd., Kawasaki, both of Japan

[21] Appl. No.: 686,711

[22] Filed: Jul. 25, 1996

Related U.S. Application Data

[62] Division of Ser. No. 528,093, Sep. 14, 1995, Pat. No. 5,604,065.

[30] Foreign Application Priority Data

| | | | |
|---|---|---|---|
| Sep. 14, 1994 | [JP] | Japan | 6-247261 |
| Sep. 14, 1994 | [JP] | Japan | 6-247262 |
| Sep. 11, 1995 | [JP] | Japan | 7-258173 |
| Sep. 11, 1995 | [JP] | Japan | 7-258174 |

[51] Int. Cl.$^6$ .................................... C07C 211/54

[52] U.S. Cl. .................................... 564/426

[58] Field of Search .................................... 564/426

[56] References Cited

U.S. PATENT DOCUMENTS 5,547,792 8/1996 Shimada et al. .................... 430/59

*Primary Examiner*—Richard L. Raymond

*Attorney, Agent, or Firm*—Oblon, Spivak, McClelland, Maier & Neustadt, P.C.

[57] ABSTRACT

An electrophotographic photoconductor includes an electroconductive substrate, and a photoconductive layer formed thereon containing at least one tertiary amine compound of formula (I) as an effective component:

(I)

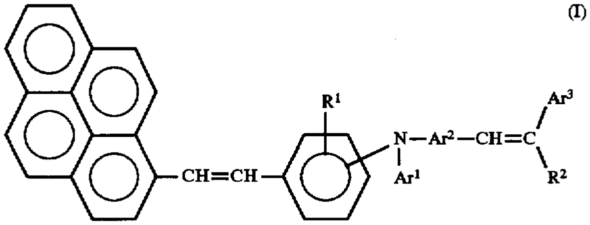

wherein $Ar^1$ and $Ar^3$ each is an aryl group which may have a substituent; $Ar^2$ is a bivalent group of a carboxylic aromatic compound or a bivalent group of a heterocyclic compound; $R^1$ is a hydrogen atom, an alkyl group which may have a substituent or an alkoxy group which may have a substituent; and $R^2$ is a hydrogen atom, an alkyl group which may have a substituent or an aryl group which may have a substituent. A novel triphenylamine compound for use in the electrophotographic photoconductor is provided.

6 Claims, 4 Drawing Sheets

TRIPHENYLAMINE COMPOUND FOR USE IN ELECTROPHOTOGRAPHIC PHOTOCONDUCTORS

This is a Division of Application Ser. No. 08/528,093 filed Sep. 14, 1995, now U.S. Pat. No. 5,604,065.

BACKGROUND OF THE INVENTION

1. Field of the Invention

The present invention relates to an electrophotographic photoconductor comprising an electroconductive substrate and a photoconductive layer formed thereon comprising at least one tertiary amine compound as an effective component. In addition, the present invention also relates to a triphenylamine compound serving as a photoconductive material in the above-mentioned electrophotographic photoconductor.

2. Discussion of Background

Conventionally, inorganic materials such as selenium, cadmium sulfide and zinc oxide are used as photoconductive materials in an electrophotographic photoconductor for use with the electrophotographic process. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electric charge of the exposed areas, so that a latent electrostatic image is formed on the photoconductor. The thus formed latent electrostatic image is developed into a visible image by toner particles comprising a coloring agent such as a dye and a pigment, and a binder agent such as a polymeric material.

Fundamental characteristics required for the photoconductor for use in such an electrophotographic process are: (1) chargeability to an appropriate potential in the dark, (2) minimum dissipation of electric charge in the dark, and (3) rapid dissipation of electric charge when exposed to light.

However, while the above-mentioned inorganic materials have many advantages, they have several shortcomings from the viewpoint of practical use.

For instance, a selenium photoconductor, which is widely used at present, satisfies the above-mentioned requirements (1) to (3) completely, but it has the shortcomings that its manufacturability conditions are difficult and, accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be obtained by coating a dispersion prepared by dispersing in a binder resin cadmium sulfide particles and zinc oxide particles, respectively. However, they are poor in mechanical properties, such as surface smoothness, hardness, tensile strength and wear resistance. Therefore, they cannot be used in the repeated operation.

To solve the problems of the aforementioned inorganic materials, various electrophotographic photoconductors employing organic materials have been proposed recently and some are put to practical use. For example, there are known a photoconductor comprising poly-N-vinylcarbazole and 2,4,7-trinitrofluorene-9-one, as disclosed in U.S. Pat. No. 3,484,237; a photoconductor prepared by sensitizing poly-N-vinylcarbazole with a pigment of pyrylium salt, as disclosed in Japanese Patent Publication 48-25658; a photoconductor comprising as the main component an organic pigment, as disclosed in Japanese Laid-Open Patent Application 47-37543; a photoconductor comprising as the main component a eutectic crystal complex of a dye and a resin, as disclosed in Japanese Laid-Open Patent Application 47-10735; a photoconductor prepared by sensitizing a triphenylamine compound with a sensitizer pigment, as disclosed in U.S. Pat. No. 3,180,730; a photoconductor comprising an amine derivative as a charge transporting material, as disclosed in Japanese Laid-Open Patent Application 57-195254; a photoconductor comprising poly-N-vinylcarbazole and an amine derivative as charge transporting materials, as disclosed in Japanese Laid-Open patent Application 58-1155; and a photoconductor comprising as a photoconductive material a polyfunctional tertiary amine compound, in particular, a benzidine compound, as disclosed in U.S. Pat. No. 3,265,496, Japanese Patent Publication 39-11546 and Japanese Laid-Open Patent Publication 53-27033.

Furthermore, there is known a photoconductor comprising as a photoconductive material a triphenylamine compound, as disclosed in Japanese Laid-Open Patent Applications 3-136057, 4-57056 and 4-282349. However, the triphenylamine compound for use in the above-mentioned photoconductor has no pyrenyl group.

These electrophotographic photoconductors have their own excellent characteristics and considered to be valuable for practical use. With various requirements of the electrophotographic photoconductor in electrophotography taken into consideration, however, the above-mentioned conventional electrophotographic photoconductors cannot meet all the requirements for use in electrophotography.

SUMMARY OF THE INVENTION

It is therefore a first object of the present invention to provide an electrophotographic photoconductor free from the conventional shortcomings, which can completely satisfy all the requirements of the electrophotographic process, and can be easily manufactured at relatively low cost.

A second object of the present invention is to provide a novel triphenylamine compound serving as a photoconductive material with good flexibility when used for the above-mentioned electrophotographic photoconductor, and capable of meeting the above-mentioned fundamental electrophotographic requirements of the electrophotographic process.

The first object of the present invention can be achieved by an electrophotographic photoconductor comprising an electroconductive substrate, and a photoconductive layer formed thereon comprising at least one tertiary amine compound of formula (I) as an effective component:

(I)

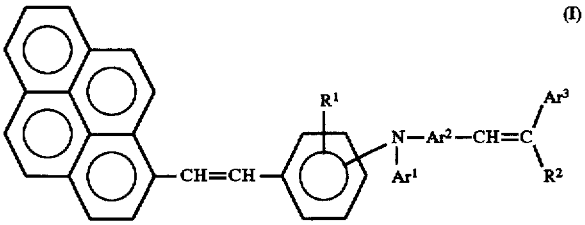

wherein $Ar^1$ and $Ar^3$ each is an aryl group which may have a substituent; $Ar^2$ is a bivalent group of a carboxylic aromatic compound or a bivalent group of a heterocyclic compound; $R^1$ is a hydrogen atom, an alkyl group which may have a substituent or an alkoxyl group which may have a substituent; and $R^2$ is a hydrogen atom, an alkyl group which may have a substituent or an aryl group which may have a substituent.

In the above-mentioned formula (I), it is preferable that the alkyl group represented by $R^1$ or $R^2$, and the alkoxy group represented by $R^1$ have 1 to 12 carbon atoms.

The second object of the present invention can be achieved by a triphenylamine compound of formula (II):

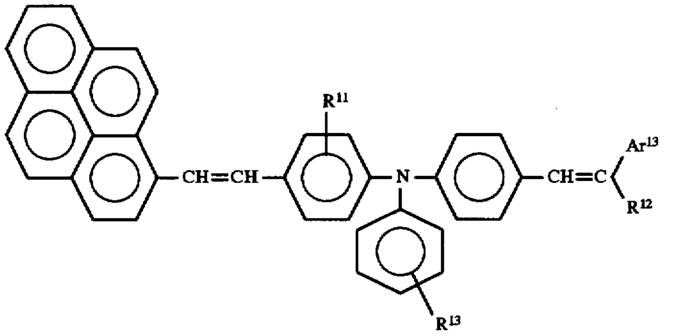

(II)

wherein $Ar^{13}$ is an aryl group which may have a substituent; $R^{11}$ and $R^{13}$ each is a hydrogen atom, an alkyl group or an alkoxy group; and $R^{12}$ is a hydrogen atom, an alkyl group which may have a substituent or an aryl group which may have a substituent.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
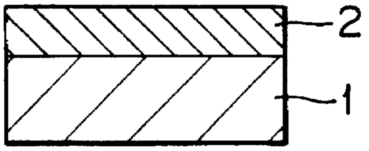
FIG. 1 is a schematic cross-sectional view of a first example of an electrophotographic photoconductor according to the present invention.

The electrophotographic photoconductor according to the present invention comprises an electroconductive substrate, and a photoconductive layer formed thereon comprising at least one tertiary amine compound of formula (I) as an effective component. The tertiary amine compound of formula (I) for use in the photoconductive layer is a novel compound, and can be synthesized from a corresponding amino compound through the combination of N-aryl substitution reaction and N-pyrenyl substitution reaction. Both reactions are generally carried out by using a corresponding halide.

The N-aryl substitution is commonly carried out by the Ullmann reaction. There can be used a solvent such as N,N-dimethylformamide, nitrobenzene, dimethyl sulfoxide or dichlorobenzene. A basic compound such as potassium carbonate, sodium carbonate, sodium hydrogencarbonate or hydrogenated sodium is used as a neutralizing agent in the reaction. The reaction is carried out in a solvent or without solvent at 160° to 250° C. In the case of poor reactivity, the reaction may be carried out in an autoclave at a higher temperature. Furthermore, it may be advantageous that the reaction be carried out with the addition of a catalyst such as copper powder, copper oxide, or halogenated copper if necessary.

Examples of the aryl group represented by $Ar^1$, $Ar^3$ and $R^2$ in the formula (I) include a non-condensed hydrocarbon group and a condensed polycyclic hydrocarbon group.

Specific examples of the non-condensed hydrocarbon group are phenyl group, biphenyl group and terphenyl group.

Specific examples of the condensed polycyclic hydrocarbon group, preferably having 18 carbon atoms or less for ring formation are pentalenyl group, indenyl group, naphthyl group, azulenyl group, heptalenyl group, biphenylenyl group, as-indacenyl group, fluorenyl group, s-indacenyl group, acenaphthylenyl group, pleiadenyl group, acenaphthenyl group, phenalenyl group, phenanthryl group, anthryl group, fluoranthenyl group, acephenanthrylenyl group, aceanthrylenyl group, triphenylenyl group, pyrenyl group, chrysenyl group and naphthacenyl group.

Specific examples of the bivalent group of carbocyclic aromatic compound represented by $Ar^3$ include a bivalent group of a monocyclic hydrocarbon compound such as benzene; a bivalent group of non-condensed polycyclic hydrogen compounds such as biphenyl, polyphenyl, diphenylalkane, diphenyalkene, diphenylalkyne, triphenylmethane, distyrylbenzene, 1,1-diphenylcycloalkane, polyphenylalkane and polyphenylalkene; a bivalent group of the same condensed polycyclic hydrocarbon compounds as described in the examples of $Ar^1$; and a bivalent group of a ring assemblies hydrocarbon compound such as 9,9-diphenylfluorene.

Specific examples of the bivalent group of heterocyclic compound represented by $Ar^2$ include a bivalent group of heterocyclic compounds such as carbazole, dibenzofuran, dibenzothiophene, oxadiazole and thiadiazole.

When $Ar^1$, $Ar^3$ and $Ar^2$ each represents an aryl group, the aryl group may have a substituent. Examples of the substituent are as follows:

(1) A halogen atom, cyano group and nitro group.

(2) A straight chain or branched chain alkyl group, preferably having 1 to 12 carbon atoms, more preferably 1 to 8 carbon atoms, and further preferably 1 to 4 carbon atoms, which may have a substituent such as a fluorine atom, hydroxyl group, cyano group, an alkoxyl group having 1 to 4 carbon atoms, or a phenyl group which may have a substituent selected from the group consisting of a halogen atom, an alkyl group having 1 to 4 carbon atoms, and an alkoxyl group having 1 to 4 carbon atoms.

Specific examples of the above-mentioned unsubstituted or substituted alkyl groups include methyl group, ethyl group, n-propyl group, i-propyl group, t-butyl group, s-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

(3) An alkoxy group represented by $-OR^3$, in which $R^3$ represents the same alkyl group which may have a substituent as defined in (2).

Specific examples of the above-mentioned unsubstituted or substituted alkoxy group include methoxy group, ethoxy group, n-propoxy group, i-propoxy group, t-butoxy group, n-butoxy group, s-butoxy group, i-butoxy group, 2-hydroxyethoxy group, 2-cyanoethoxy group, benzyloxy group, 4-methylbenzyloxy group and trifluoromethoxy group.

(4) An aryloxy group, in which an aryl group represents, for example, a phenyl group or a naphthyl group. The above aryloxy group may have a substituent such as an alkoxy group having 1 to 4 carbon atoms, an alkyl group having 1 to 4 carbon atoms or a halogen atom.

Specific examples of the above-mentioned unsubstituted or substituted aryloxy group include phenoxy group, 1-naphthyloxy group, 2-naphthyloxy group, 4-methylphenoxy group, 4-methoxyphenoxy group, 4-chlorophenoxy group and 6-methyl-2-naphthyloxy group.

(5) An alkylmercapto group or arylmercapto group.

Specific examples of the alkylmercapto group and arylmercapto group are methylthio group, ethylthio group, phenylthio group and p-methylphenylthio group.

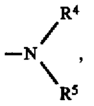 (6)

in which $R^4$ and $R^5$ independently represent a hydrogen atom, the same alkyl group which may have a substituent as defined in (2) or an aryl group which may have a substituent. As the aryl group, phenyl group, biphenyl group or naphthyl group can be employed, which may have a substituent such as an alkoxyl group having 1 to 4 carbon atoms, an alkyl group having 1 to 4 carbon atoms or a halogen atom. $R^4$ and $R^5$ may form a ring in combination, or in combination with carbon atoms on the aryl group.

Specific examples of the group represented by

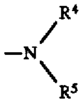

include amino group, diethylamino group, N-methyl-N-phenylamino group, N,N-diphenylamino group, N,N-di(p-tolyl)amino group, dibenzylamino group, piperidino group, morpholino group and julolidyl group.

(7) An alkylenedioxy group such as methylenedioxy group, or an alkylenedithio group such as methylenedithio group.

When $R^1$ and $R^2$ each is an alkyl group is the formula (I), the same examples of the alkyl group as described in the above-mentioned group (2) can be employed. In the case where $R^1$ represents an alkoxyl group, the same examples of the alkoxyl group as described in the above-mentioned (3) can be employed.

Specific examples of the tertiary amine compound of formula (I) for use in the present invention are shown in the following Table 1:

TABLE 1

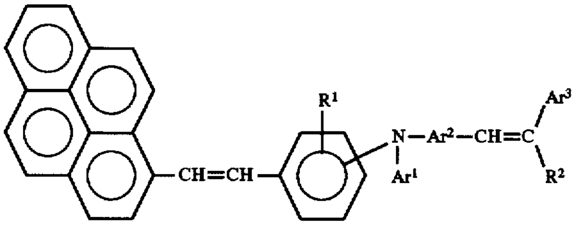

| Compound No. | $Ar^1$ | $Ar^2$ | $Ar^3$ | $R^1$ | $R^2$ |
|---|---|---|---|---|---|
| 1 | 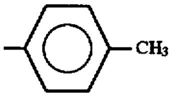 | 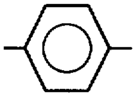 | 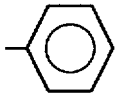 | H | H |
| 2 | 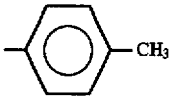 | 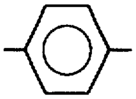 | 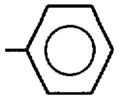 | H | 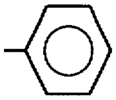 |

TABLE 1-continued
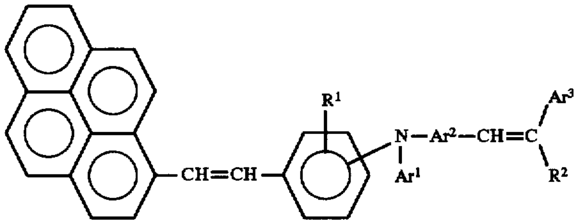
| Compound No. | Ar¹ | Ar² | Ar³ | R¹ | R² |
|---|---|---|---|---|---|
| 3 | 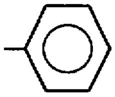 | 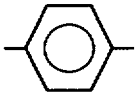 | 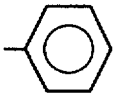 | H | 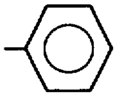 |
| 4 | 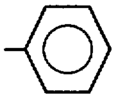 | 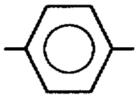 | 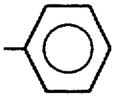 | H | H |
| 5 | 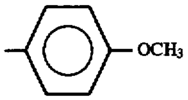 | 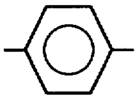 | 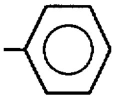 | H | H |
| 6 | 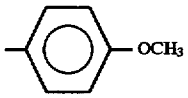 | 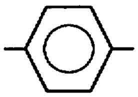 | 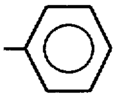 | H | 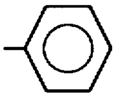 |
| 7 | 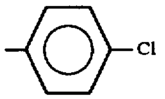 | 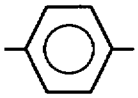 | 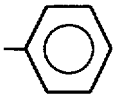 | H | 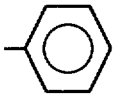 |
| 8 | 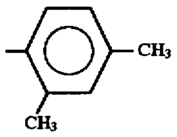 | 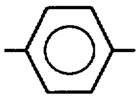 | 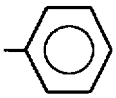 | H | 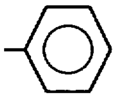 |
| 9 | 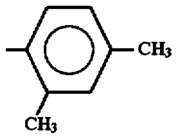 | 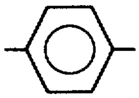 | 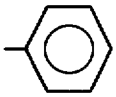 | H | H |
| 10 | 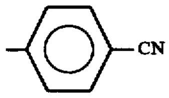 | 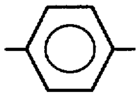 | 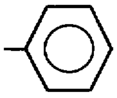 | H | 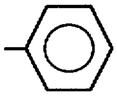 |
| 11 | 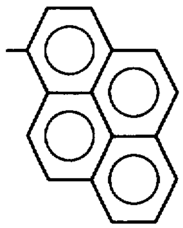 | 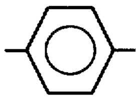 | 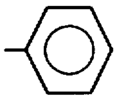 | H | 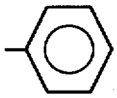 |
| 12 | 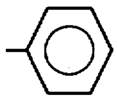 | 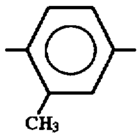 | 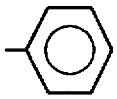 | H | 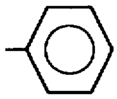 |

TABLE 1-continued
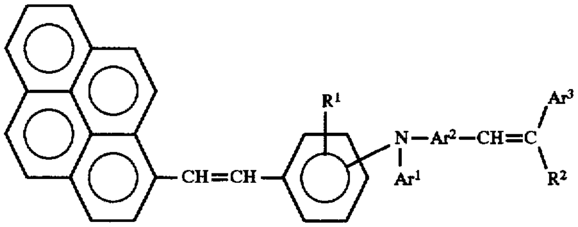
| Compound No. | $Ar^1$ | $Ar^2$ | $Ar^3$ | $R^1$ | $R^2$ |
|---|---|---|---|---|---|
| 13 | 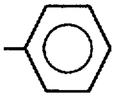 | 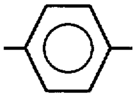 | 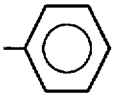 | 3-$CH_3$ | 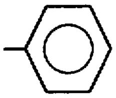 |
| 14 | 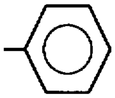 | 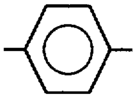 | 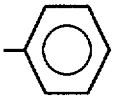 | H | $CH_3$ |
| 15 | 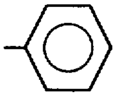 | 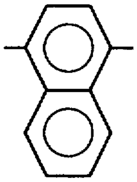 | 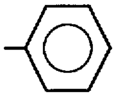 | H | 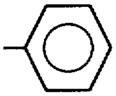 |
| 16 | 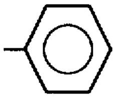 | 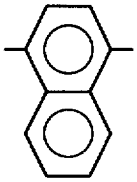 | 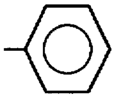 | H | H |
| 17 | 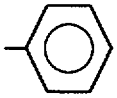 | 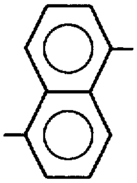 | 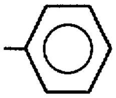 | H | 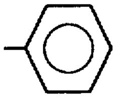 |
| 18 | 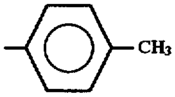 | 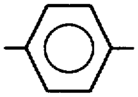 | 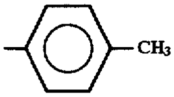 | H | 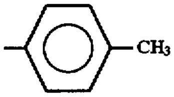 |
| 19 | 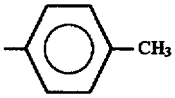 | 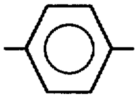 | 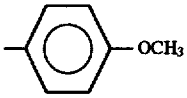 | H | H |
| 20 | 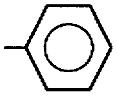 | 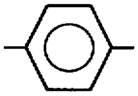 | 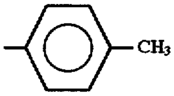 | H | 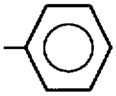 |
| 21 | 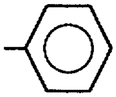 | 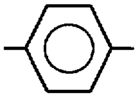 | 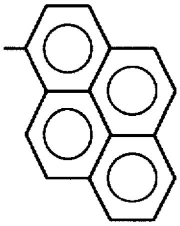 | H | H |

TABLE 1-continued

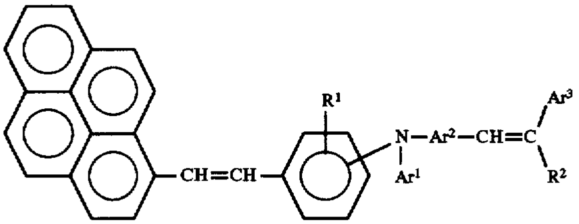

| Compound No. | $Ar^1$ | $Ar^2$ | $Ar^3$ | $R^1$ | $R^2$ |
|---|---|---|---|---|---|
| 22 | 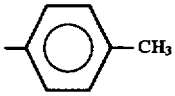 | 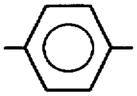 | 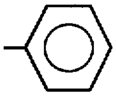 | H | 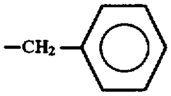 |
| 23 | 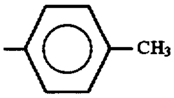 | 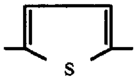 | 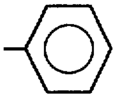 | H | 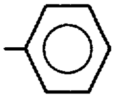 |

Of the tertiary amine compounds of formula (I), the following triphenylamine compound of formula (II), which can also be employed as the photoconductive material in the electrophotographic photoconductor of the present invention, is a novel compound:

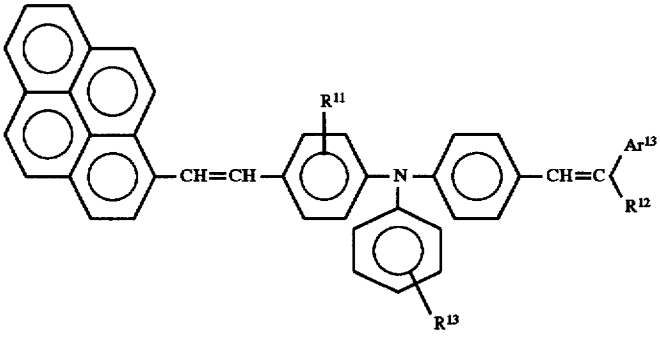

(II)

wherein $Ar^{13}$ is an aryl group which may have a substituent; $R^{11}$ and $R^{13}$ each is a hydrogen atom, an alkyl group or an alkoxyl group; and $R^{12}$ is a hydrogen atom, an alkyl group which may have a substituent, or an aryl group which may have a substituent.

The above-mentioned novel triphenylamine compound of formula (II) can be prepared in such a manner that a corresponding amino compound is subjected to an N-arylation reaction in accordance with the Ullmann reaction to obtain a triphenylamine compound, the triphenylamine compound thus obtained is subjected to formylation and then to a modified Wittig reaction with a corresponding phosphonate, and the thus obtained compound is further subjected to formylation and to the modified Wittig reaction with pyrenylmethyl phosphonate. The formylation is generally carried out in accordance with the Vilsmeier reaction.

For instance, a triphenylamine compound of the following formula (III) is subjected to formylation by use of N,N-dimethylformaldehyde and phosphorus oxychloride to obtain an aldehyde compound:

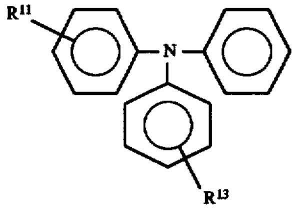

(III)

wherein $R^{11}$ and $R^{13}$ each is a hydrogen atom, an alkyl group or an alkoxyl group.

The aldehyde compound thus obtained is allowed to react with phosphonate of the following formula (IV), so that an arylvinyl triphenylamine compound of formula (V) can be obtained:

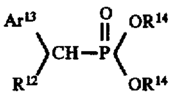

(IV)

wherein $Ar^{13}$ is an aryl group which may have a substituent; $R^{12}$ is a hydrogen atom, an alkyl group which may have a substituent or an aryl group which may have a substituent; and $R^{14}$ is a lower alkyl group:

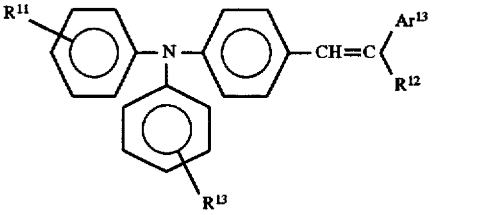

(V)

wherein $Ar^{13}$ is an aryl group which may have a substituent; $R^{11}$ and $R^{13}$ each is a hydrogen atom, an alkyl group or an alkoxy group; and $R^{12}$ is a hydrogen atom, an alkyl group which may have a substituent, or an aryl group which may have a substituent.

The above-mentioned arylvinyl triphenylamine compound and the method of manufacturing the arylvinyl triphenylamine compound are described in Japanese Laid-Open Patent Applications 58-189145, 58-198425, 59-95245, 59-98041, 59-190931, 59-191763, 59-67250, 59-67251, 59-196845, 59-216853, 60-94967, 60-94461 and 60-94462; and U.S. Pat. Nos. 4,892,949 and 4,859,556.

Furthermore, the arylvinyl triphenylamine compound of formula (V) is subjected to formylation similarly, the allowed to react with a pyrenylmethyl phosphonate of the following formula (VI), so that a triphenylamine compound of formula (II) according to the present invention can be obtained:

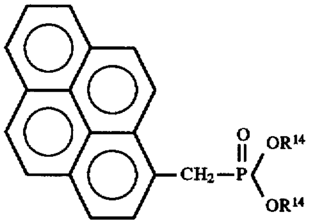

(VI)

wherein $R^{14}$ is a lower alkyl group.

To synthesize the triphenylamine compound of formula (II), the reaction by use of the phosphonate of formula (VI) may be carried out before the reaction by use of the phosphonate of formula (IV).

The aforementioned condensation reaction of the aldehyde compound with the phosphonate is known as the modified Wittig reaction. It is preferably that this modified Wittig reaction by carried out in the presence of a basic catalyst.

Examples of the basic catalyst used in the modified Wittig reaction are potassium hydroxide, sodium amide, and alcoholate such as sodium methylate, potassium methylate, and potassium-t-butoxide.

Examples of the reaction solvent are methanol, ethanol, propanol, toluene, xylene, dioxane, N,N-dimethylformamide, dimethyl sulfoxide and tetrahydrofuran.

The reaction temperature can be determined in a wide range depending on the following factors: (1) the stability of the employed solvent to the basic catalyst, (2) the reactivity of condensation components, and (3) the reactivity of the basic catalyst as a condensation agent in the solvent. For example, the reaction may be carried out at a temperature in a range from room temperature to 100° C., preferably from room temperature to 80° C. when a polar solvent is employed. When curtailment of the reaction time is desired or the condensation agent with a low activity is employed, the reaction may be carried out at a temperature higher than the above-mentioned temperature.

The phosphonate represented by formula (IV) or (VI), serving as a raw material for producing the triphenylamine compound of formula (II), can be readily obtained by allowing a corresponding halide to react with a trialkyl phosphite directly or in an organic solvent such as toluene, xylene or N,N-dimethylformamide with the application of heat thereto.

In the formula (II), the aryl group represented by $Ar^{13}$ may be phenyl group, naphthyl group, and biphenylyl group, which may be substituted with an alkyl group having 1 to 4 carbon atoms or with an alkoxyl group having 1 to 4 carbon atoms.

Specific examples of the unsubstituted or substituted aryl group represented by $Ar^{13}$ are phenyl group, tolyl group, methoxyphenyl group, biphenylyl group and naphthyl group.

$R^{11}$ and $R^{13}$ each is a hydrogen atom, an alkyl group or an alkoxy group as mentioned previously. The alkyl group represented by $R^{11}$ or $R^{13}$ may be an alkyl group having 1 to 4 carbon atoms, such as methyl group, ethyl group, propyl group and butyl group. The alkoxy group represented by $R^{11}$ or $R^{13}$ may be an alkoxy group having 1 to 4 carbon atoms, such as methoxy group, ethoxy group, propoxy group and butoxy group.

$R^{12}$ is a hydrogen atom or an alkyl group which may have a substituent, or an aryl group which may have a substituent as mentioned previously. The alkyl group represented by $R^{12}$ may be an alkyl group having 1 to 4 carbon atoms, which may be substituted with an alkoxyl group having 1 to 4 carbon atoms.

Specific examples of the unsubstituted or substituted alkyl group represented by $R^{12}$ are methyl group, ethyl group, methoxyethyl group, and ethoxyethyl group.

The aryl group represented by $R^{12}$ may be phenyl group, naphthyl group, or biphenylyl group, which may be substituted with an alkyl group having 1 to 4 carbon atoms or with an alkoxyl group having 1 to 4 carbon atoms.

Specific examples of the unsubstituted or substituted aryl group represented by $R^{12}$ are phenyl group, tolyl group, methoxyphenyl group, biphenylyl group and naphthyl group.

The triphenylamine compound of formula (II) according to the present invention, which is remarkably effective as a photoconductive material in the electrophotographic photoconductor, is optically or chemically sensitized with a sensitizer such as a dye or Lewis acid. In particular, the triphenylamine compound of formula (II) effectively functions as a charge transporting material in a function-separating type electrophotographic photoconductor where an organic or inorganic pigment serves as a charge generating material.

The structure of the photoconductor of the present invention will now be explained in detail by referring to FIGS. 1 to 5.

In the photoconductors according to the present invention, one or more of tertiary amine compounds of formula (I) are contained in photoconductive layers 2, 2*a*, 2*b*, 2*c* and 2*d*. The tertiary amine compounds can be employed in different ways, for example, as shown in FIGS. 1 to 5.

In a photoconductor as shown in FIG. 1, a photoconductive layer 2 is formed on an electroconductive substrate 1, which photoconductive layer 2 comprises a tertiary amine compound, a sensitizing dye and a binder agent (binder resin). In this photoconductor, the tertiary amine compound works as a photoconductive material, through which charge carriers which are necessary for the light decay of the photoconductor are generated and transported. However, the tertiary amine compound itself scarcely absorbs light in the visible light range, so that it is necessary to add a sensitizing dye which absorbs light in the visible light range in order to form latent electrostatic images by use of visible light.

Figure 2:
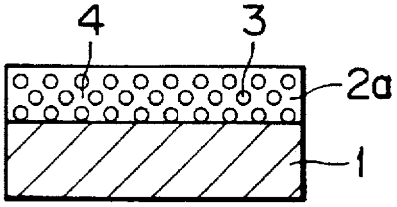
FIG. 2 is a schematic cross-sectional view of a second example of an electrophotographic photoconductor according to the present invention.

Referring to FIG. 2, there is shown a cross-sectional view of another embodiment of an electrophotographic photoconductor according to the present invention. In the figure, on an electroconductive substrate 1, there is formed a photoconductive layer 2*a* comprising a charge generating material 3 dispersed in a charge transporting medium 4 comprising a tertiary amine compound and a binder agent. In this embodiment, the tertiary amine compound and the binder agent (or a mixture of the binder agent and a plasticizer) in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is essential that the light-absorption wavelength regions of the charge generating material 3 and the tertiary amine compound not overlap in the visible light range. This is because, in order to cause the charge generating material 3 to produce charge carriers efficiently, it is necessary to allow the light to reach the surface of the charge generating material 3. The tertiary amine compounds of formula (I) scarcely absorb the light in the visible range. Therefore, especially when used in combination with the charge generating material 3 which absorbs the light in the visible region and generates charge carriers, the tertiary amine compounds can work effectively as charge transporting materials.

Figure 3:
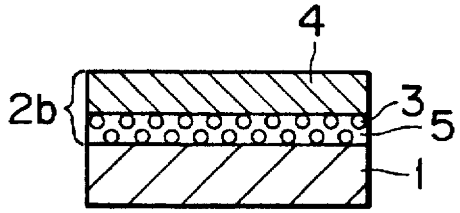
FIG. 3 is a schematic cross-sectional view of a third example of an electrophotographic photoconductor according to the present invention.

Referring to FIG. 3, there is shown a cross-sectional view of a further embodiment of an electrophotographic photoconductor according to the present invention. In the figure, there is formed on an electroconductive substrate 1 a two-layered photoconductive layer 2*b* comprising a charge generation layer 5 containing a charge generating material 3, and a charge transport layer 4 containing a tertiary amine compound.

In this photoconductor, the light which has passed through the charge transport layer 4 reaches the charge generation layer 5, where charge carriers are generated. The charge carriers which are necessary for the light decay for latent electrostatic image formation are generated by the charge generating material 3, and accepted and transported by the charge transport layer 4. In the charge transport layer 4, the tertiary amine compound mainly works to transport the charge carriers. The generation and transportation of the charge carriers are performed by the same mechanism as that in the photoconductor shown in FIG. 2.

Figure 4:
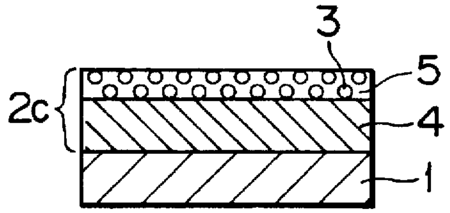
FIG. 4 is a schematic cross-sectional view of a fourth example of an electrophotographic photoconductor according to the present invention.

Referring to FIG. 4, there is shown still another embodiment of an electrophotographic photoconductor according to the present invention. In the figure, the overlaying order of a charge generation layer 5 and a charge transport layer 4 is reversed. The mechanism of the generation and transportation of charge carriers is substantially the same as that of the photoconductor shown in FIG. 3.

Figure 5:
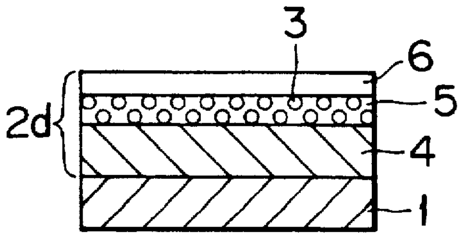
FIG. 5 is a schematic cross-sectional view of a fifth example of an electrophotographic photoconductor according to the present invention.

In the above photoconductor, a protective layer 6 may be formed on a charge generation layer 5 as shown in FIG. 5 for improving the mechanical strength thereof.

When the electrophotographic photoconductor according to the present invention as shown in FIG. 1 is prepared, one or more of tertiary amine compounds of formula (I) are dissolved in a binder resin solution, and a sensitizing dye is then added to the mixture, so that a photoconductive layer coating liquid is prepared. The thus prepared photoconductive layer coating liquid is coated on the electroconductive substrate 1 and dried, so that the photoconductive layer 2 is formed on the electroconductive substrate 1.

It is preferable that the thickness of the photoconductive layer 2 be in a range of 3 to 50 μm, more preferably in a range of 5 to 20 μm. It is preferable that the amount of the tertiary amine compound contained in the photoconductive layer 2 be in a range of 30 to 70 wt. %, more preferably about 50 wt. % of the total weight of the photoconductive layer 2.

It is preferable that the amount of the sensitizing dye contained in the photoconductive layer 2 be in a range of 0.1 to 5 wt. %, more preferably in a range of 0.5 to 3 wt. % of the total weight of the photoconductive layer 2.

Specific examples of the sensitizing dye for use in the present invention are as follows: triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; pyrylium dyes such as 2,6-diphenyl-4-(N,N-dimethylaminophenyl)thiapyrylium perchlorate and benzopyrylium salts (described in Japanese Patent Publication 48-25658); and 2,4,7-trinitro-9-fluorenone and 2,4-dinitro-9-fluorenone. These sensitizing dyes can be used alone or in combination.

The electrophotographic photoconductor shown in FIG. 2 can be obtained by dispersing finely-divided particles of the charge generating material 3 in a solution in which one or more of the tertiary amine compounds and the binder agent are dissolved, coating the above-prepared dispersion on the electroconductive substrate 1 and then drying the same to form the photoconductive layer 2*a*.

It is preferably that the thickness of the photoconductive layer 2*a* be in a range of 3 to 50 μm, more preferably in a range of 5 to 20 μm. It is preferable that the amount of the tertiary amine compound contained in the photoconductive layer 2*a* be in a range of 10 to 95 wt. %, more preferably in a range of 30 to 90 wt. % of the total weight of the photoconductive layer 2*a*.

It is preferable that the amount of the charge generating material 3 contained in the photoconductive layer 2*a* be in a range of 0.1 to 50 wt. %, more preferably in a range of 1 to 20 wt. % of the total weight of the photoconductive layer 2*a*.

Specific examples of the charge generating material 3 are as follows: inorganic pigments such as selenium, selenium—tellurium, cadmium sulfide, cadmium sulfide—selenium and α-silicon (amorphous silicon); and organic pigments, such as azo pigments including C.I. Pigment Blue 25 (C.I. 21180), C.I. Pigment Red (C.I. 21200), C.I. Acid Red 52 (C.I. 45100), C.I. Basic Red 3 (C.I. 45210), an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiphene skeleton ((Japanese Laid-Open Patent Application 54-21728), an azo pigment having an oxadiazole skeleton (Japanese Laid-Open Patent Application 54-12742), an azo pigment having a fluorenone skeleton ((Japanese Laid-Open Patent Application 54-22834), an azo pigment having a bisstilbene skeleton (Japanese Laid-Open Patent Application 54-1773), an azo pigment having a distyryl oxadiazole skeleton (Japanese Laid-Open Patent Application 54-2129), and an azo pigment having a distyryl carbazole skeleton (Japanese Laid-Open Patent Application 54-14967); phthalocyanine pigments including C.I. Pigment Blue 16 (C.I. 74100); indigo pigments including C.I. Vat Brown 5 (C.I. 73410) and C.I. Vat Dye (C.I. 73030); and perylene pigments including Algol Scarlet B (made by Bayer Co., Ltd.) and Indanthrene Scarlet R (made by Bayer Co., Ltd.). These charge generating materials may be used alone or in combination.

The electrophotographic photoconductor shown in FIG. 3 can be obtained as follows:

The charge generating material 3 may be vacuum-deposited deposited on the electroconductive substrate 1. Alternatively, the dispersion in which finely-divided particles of the charge generating material 3 are dispersed in an appropriate solvent together with the binder agent when necessary, may be coated on the electroconductive substrate 1 and dried, so that the charge generation layer 5 is formed on the electroconductive substrate 1. When necessary, the charge generation layer 5 is subjected to surface treatment by buffing and adjusting of the thickness thereof. On the thus formed charge generation layer 6, a coating liquid in which one or more of tertiary amine compounds and the binder agent are dissolved is coated and dried, so that the charge transport layer 4 is formed on the charge generation layer 5. In the charge generation layer 5, the same charge generating materials as employed in the previously mentioned photoconductive layer 2*a* can be used.

The thickness of the charge generation layer 5 is preferably 5 μm or less, more preferably 2 μm or less. It is preferably that the thickness of the charge transport layer 4 be in a range of 3 to 50 μm, more preferably in a range of 5 to 20 μm. When the charge generation layer 5 is obtained by coating of the dispersion in which finely-divided particles of the charge generation material 5 are dispersed in the binder agent, it is preferably that the amount of finely-divided particles of the charge generating material 3 contained in the charge generation layer 5 to be in a range of 10 to 95 wt. %, more preferably in a range of about 50 to 90 wt. % of the total weight of the charge generation layer 5. It is preferable that the amount of the tertiary amine compound contained in the charge transport layer 4 be in a range of 10 to 95 wt. %, more preferably in a range of 30 to 90 wt. % of the total weight of the charge transport layer 4.

The electrophotographic photoconductor shown in FIG. 4 can be obtained as follows:

A coating liquid in which the tertiary amine compound and the binder agent are dissolved is coated on the electroconductive substrate 1 and dried to form the charge transport layer 4. On the thus formed charge transport layer 4, a dispersion prepared by dispersing finely-divided particles of the charge generating material 3 in a solvent, in which the binder agent is dissolved when necessary, is coated by spray coating and dried to form the charge generation layer 5 on the charge transport layer 4. The amount ratio of the tertiary amine compound in the charge transport layer 4, and that of the charge generating material 3 in the charge generation layer 5 are the same as previously described in FIG. 3.

Further, the protective layer 6 can be provided on the charge generation layer 5 by coating an appropriate resin solution by spray coating as shown in FIG. 5. As a resin to be employed in the protective layer 6, any binder agents to be described later can be used.

Specific examples of the material for the electroconductive substrate 1 of the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl copolymers such as polyvinylketone, polystyrene, poly-N-vinylcarbazole and polyacrylamide. All the resins having insulating properties and adhesive properties can be employed.

Some plasticizers may be added to the above-mentioned binder agent, when necessary. Examples of such plasticizers are halogenated paraffin, dimethylnaphthalene and dibutyl phthalate.

Furthermore, in the electrophotographic photoconductors according to the present invention, an adhesive layer or a barrier layer can be interposed between the electroconductive substrate and the photoconductive layer when necessary. Examples of the material for use in the adhesive layer or barrier layer are polyamide, nitrocellulose and aluminum oxide. It is preferable that the thickness of the adhesive layer or barrier layer be 1 μm or less.

When copying is performed by use of the photoconductor according to the present invention, the surface of the photoconductor is charged uniformly in the dark to a predetermined polarity. The uniformly charged photoconductor is exposed to a light image, so that a latent electrostatic image is formed on the photoconductor. The thus formed latent electrostatic image is developed by a developer to a visible image, and the developed image can be transferred to a sheet of paper when necessary.

The electrophotographic photoconductors according to the present invention have the advantages in that the photosensitivity is high and the flexibility is improved.

Other features of this invention will become apparent in the course of the following description of exemplary embodiments, which are given for illustration of the invention and are not intended to be limiting thereof.

SYNTHESIS EXAMPLE 1

[Synthesis of 4-(β-1-pyrenylvinyl)-4'-styryltriphenylamine (tertiary amine compound No. 4)]

45.6 g (0.18 mol) of 1-chloromethylpyrene was added to 180 g (1.08 mol) of triethyl phosphite, and the mixture was stirred at 140° C. for 5 hours. The mixture was cooled to 50° C., and 200 ml of hexane was added thereto. After the mixture was ice-cooled, the resulting crystals were obtained by filtration, washed with hexane and then recrystallized from a mixed solvent of ethyl acetate and hexane. Thus, 52.4 g of diethyl 1-pyrenylmethyl phosphonate was obtained in a yield of 81.8%. The melting point of the above-mentioned compound was 115.0° to 116.0° C.

A mixture of 17.6 g (0.05 mol) of the above obtained diethyl 1-pyrenylmethyl phosphonate and 18.7 g (0.05 mol) of 4-formyl-4'-styryltriphenylamine was added to 250 ml of N,N-dimethylformamide, and the thus obtained mixture was cooled to 10° C. or less. After 6.8 g (0.06 mol) of potassium tert-butoxide was added to the above mixture with the temperature being maintained at 10° C. or less, the mixture was heated to room temperature and stirred for one hour. The reaction mixture was added to 500 ml of methanol, and the resulting crystals were obtained by filtration. The crystals thus obtained were thoroughly washed with methanol, and recrystallized from toluene three times, so that 11.4 g of 4-(β-1-pyrenylvinyl)-4'-styryltriphenylamine was obtained in a yield of 39.9%. The melting point of the above-mentioned compound was 278.0° to 279.0° C.

The results of the elemental analysis of the compound were as follows:

| | % C | % H | % N |
|---|---|---|---|
| Calculated | 92.11 | 5.45 | 2.44 |
| Found | 92.42 | 5.68 | 2.38 |

The above calculation was based on the formula for 4-(β-1-pyrenylvinyl)-4'-styryltriphenylamine of $C_{44}H_{31}N$.

Figure 6:
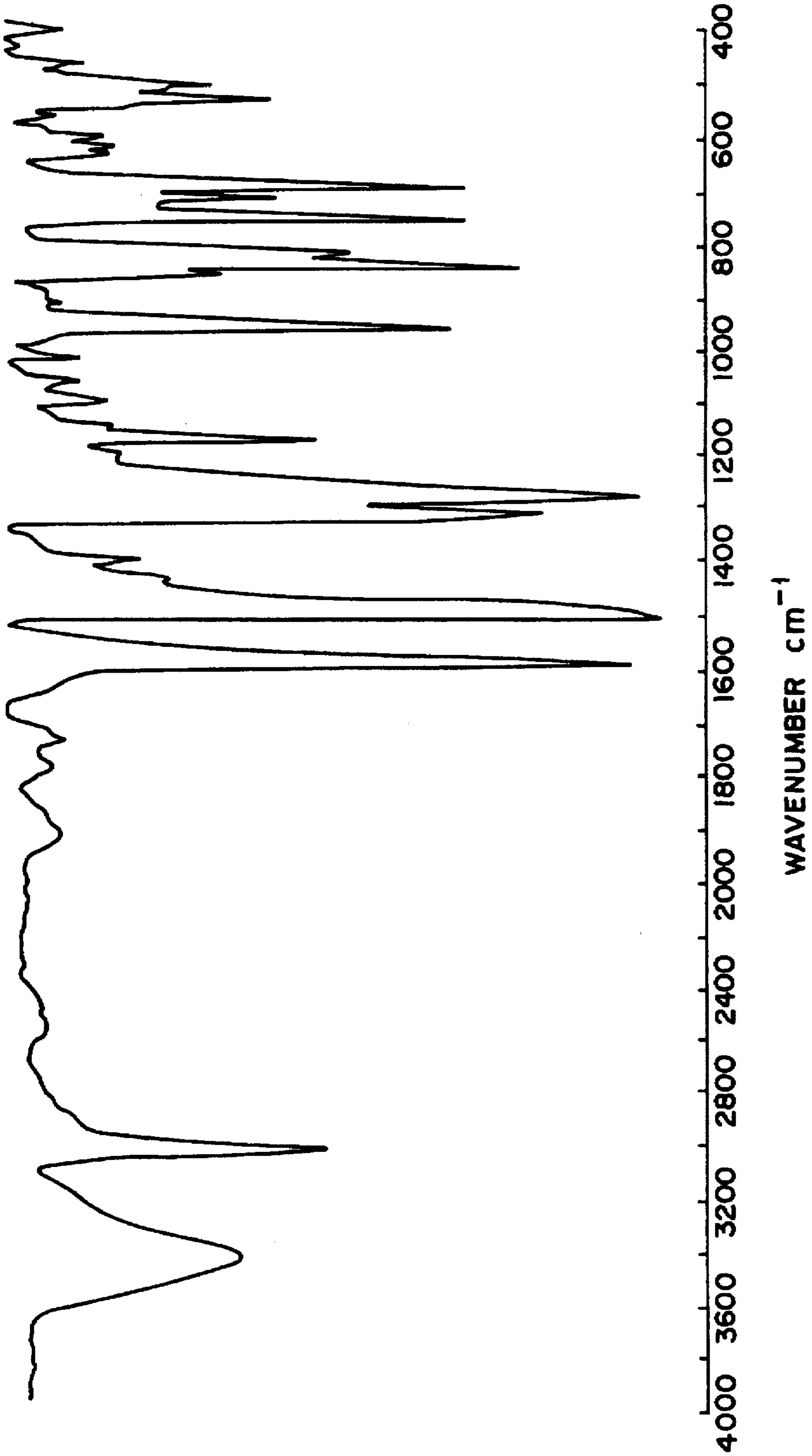
FIG. 6 is an IR spectrum of 4-(β-1-pyrenylvinyl)-4'-styryltriphenylamine by use of a KBr tablet.

FIG. 6 shows an IR spectrum of the above compound taken by use of a KBr tablet.

SYNTHESIS EXAMPLE 2

[Synthesis of 4-methoxy-4'-(β-1-pyrenylvinyl)-4"-(β-phenylstyryl)triphenylamine]

A mixture of 17.6 g (0.05 mol) of diethyl 1-pyrenylmethyl phosphonate obtained in Synthesis Example 1 and 24.0 g (0.05 mol) of 4-formyl-4-methoxy-4'-(β-phenylstyryl) triphenylamine was added to 400 ml of N,N-dimethylformamide, and the thus obtained mixture was cooled to 10° C. or less. After 8.4 g (0.075 mol) of potassium tert-butoxide was added to the above mixture with the temperature being maintained at 10° C. or less, the mixture was heated to room temperature and stirred for one hour. The reaction mixture was added to 800 ml of methanol, and the resulting crystals were obtained by filtration. The crystals thus obtained were purified by subjecting to silica gel column chromatography using a mixed solvent of toluene and hexane with a volume ratio of 1:1 as an eluting solution, so that 22.1 g of 4-methoxy-(β-1-pyrenylvinyl)-4"-(β-phenylstyryl)-triphenylamine was obtained in a yield of 65.1%. The melting point of the above-mentioned compound was 199.0° to 20.10° C.

The results of the elemental analysis of the compound were as follows:

| | % C | % H | % N |
|---|---|---|---|
| Calculated | 90.10 | 5.49 | 2.06 |
| Found | 90.34 | 5.66 | 2.22 |

The above calculation was based on the formula for 4-methoxy-(β-1-pyrenylvinyl)-4"-(β-phenylstyryl)-triphenylamine of $C_{51}H_{97}NO$.

Figure 7:
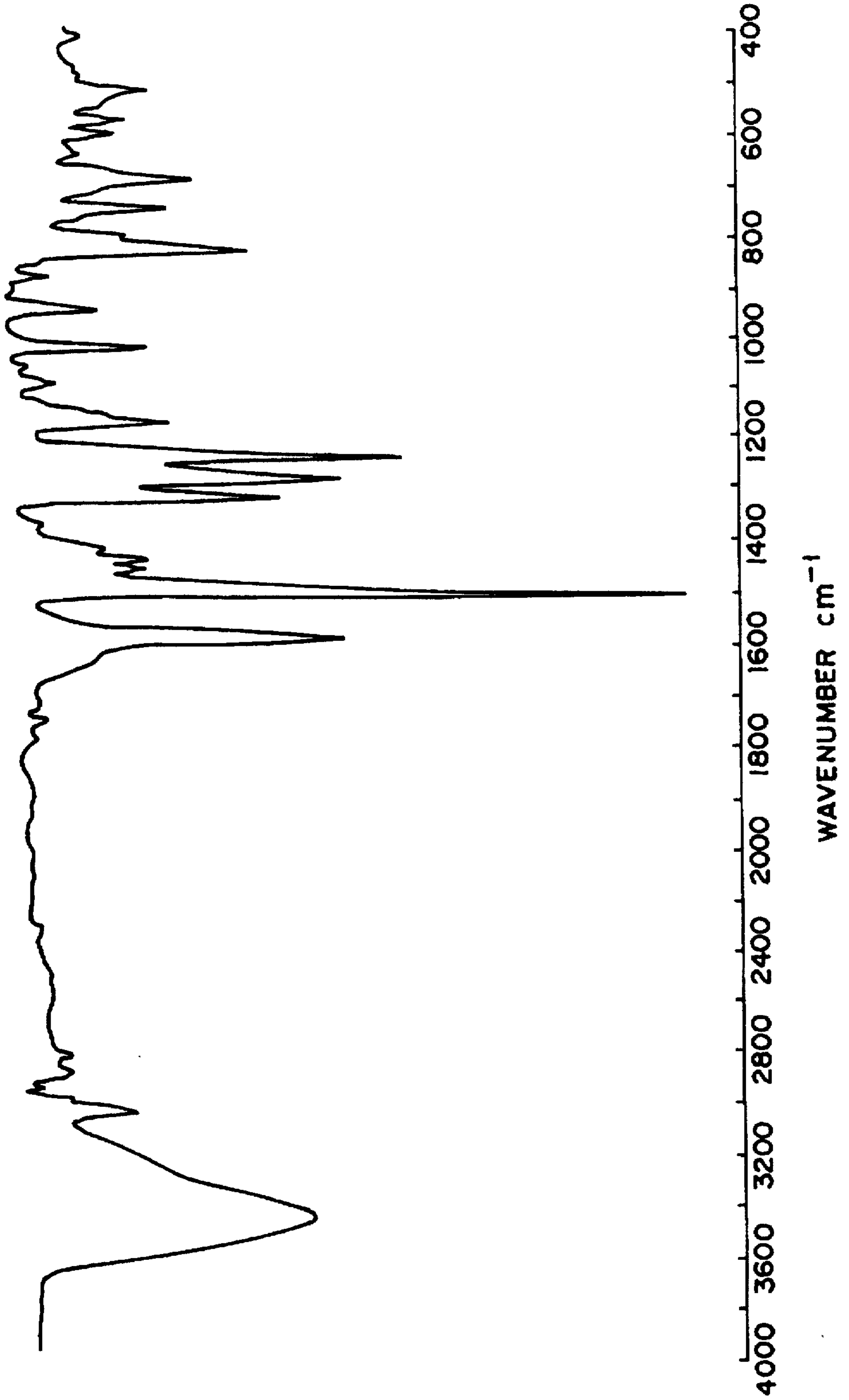
FIG. 7 is an IR spectrum of 4-methoxy-4'-(β-1-pyrenylvinyl) -4"-(β-phenylstyryl)triphenylamine by use of a KBr tablet.

FIG. 7 shows an IR spectrum of the above compound taken by use of a KBr tablet.

SYNTHESIS EXAMPLE 3

[Synthesis of 4-(β-1-pyrenylvinyl)-4'-(β-phenylstyryl) triphenylamine (tertiary amine compound No. 3)]

A mixture of 0.62 g (1.8 mmol) of diethyl 1-pyrenylmethyl phosphonate obtained in Synthesis Example 1 and 0.80 (1.8 mmol) of 4-formyl-4'(β-phenylstyryl)-triphenylamine was added to 10 ml of N,N-dimethylformamide. 0.51 g (2.6 mmol) of a 28% methanol solution containing sodium methoxide was added dropwise to the above mixture at room temperature. After the completion of addition, the mixture was stirred for 3 hours at room temperature. The reaction mixture was poured into water, and the resulting crystals were obtained by filtration. The crystals thus obtained were purified by subjecting to silica gel column chromatography using a mixed solvent of toluene and n-hexane with a volume ratio of 1:2 as an eluting solution, so that 0.76 g of 4-(β-1-pyrenylvinyl)-4'-(β-phenylstyryl) triphenylamine was obtained in a yield of 65.0%. The melting point of the above-mentioned compound was 189.0° to 190.0° C.

The results of the elemental analysis of the compound were as follows:

| | % C | % H | % N |
|---|---|---|---|
| Calculated | 92.40 | 5.44 | 2.16 |
| Found | 92.72 | 5.40 | 2.10 |

The above calculation was based on the formula for 4-(β-1-pyrenylvinyl)-4'-(β-phenylstyryl) triphenylamine of $C_{50}H_{95}N$.

Figure 8:
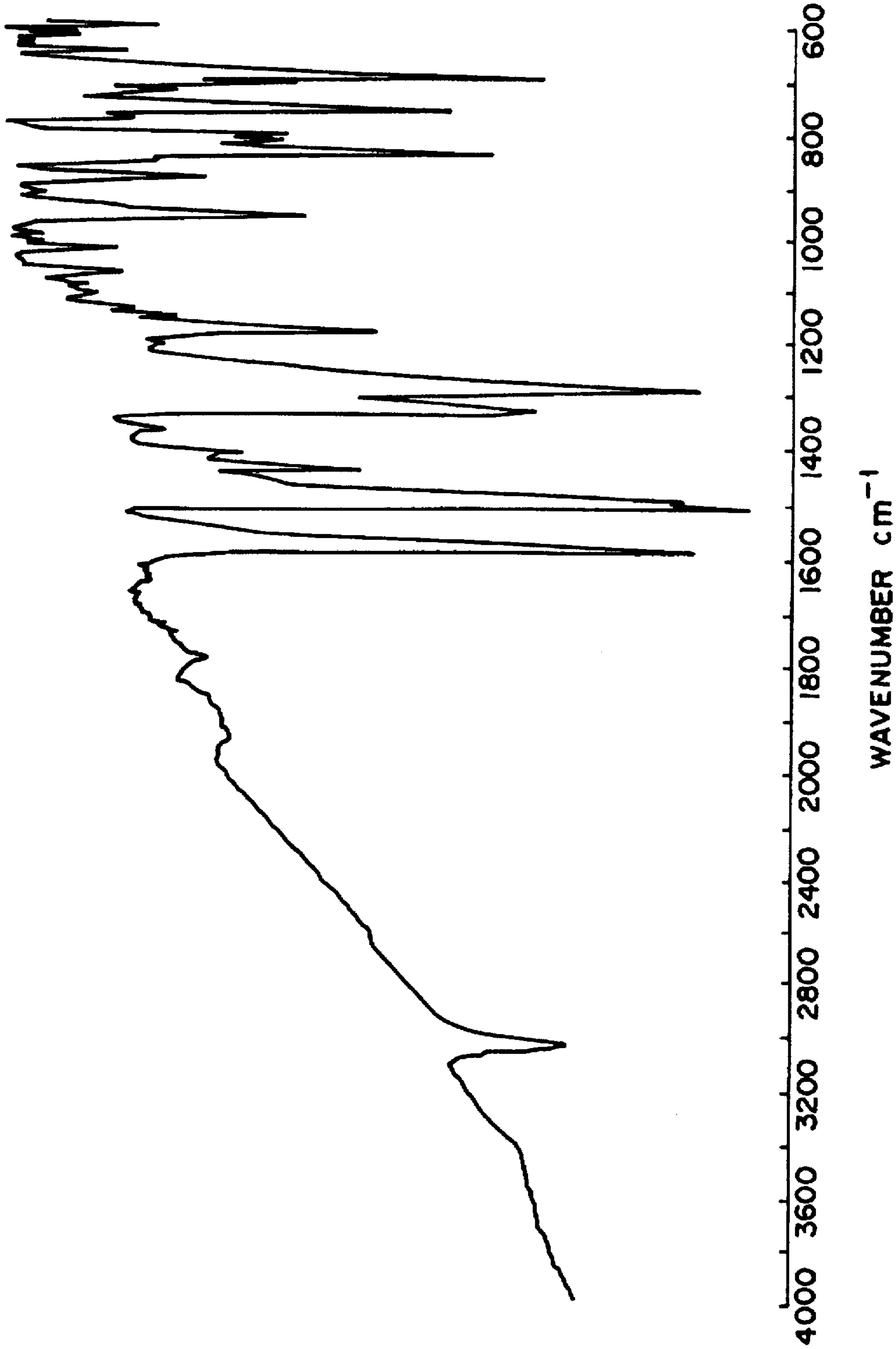
FIG. 8 is an IR spectrum of 4-(β-1-pyrenylvinyl)-4'-(β-phenylstyryl)triphenylamine by use of a KBr tablet.

FIG. 8 shows an IR spectrum of the above compound taken by use of a KBr tablet.

EXAMPLE 1

76 parts by weight of Diane Blue (C.I. Pigment Blue 25: C.I. 21180) serving as a charge generating material, 1,260 parts by weight of a 2% tetrahydrofuran solution of a polyester resin (Trademark "Vylon 200" made by Toyobo Company, Ltd.), and 3,700 parts by weight of tetrahydrofuran were dispersed and ground in a ball mill. The thus prepared dispersion was coated on an aluminum surface of an aluminum-deposited polyester film serving as an electroconductive substrate by a doctor blade, and dried at room temperature, so that a charge generation layer with a thickness of about 1 μm was formed on the electroconductive substrate.

2 parts by weight of the tertiary amine compound (tertiary amine compound No. 6 in Table 1) serving as a charge transporting material, 2 parts by weight of polycarbonate resin (Trademark "Panlite K-1300" made by Teijin Chemicals Ltd.), and 16 parts by weight of tetrahydrofuran were mixed to prepared a coating liquid for a charge transport layer. This liquid was coated on the above formed charge generation layer by a doctor blade, and dried at 80° C. for 2 minutes and then at 120° C. for 5 minutes, so that a charge transport layer with a thickness of about 20 μm was formed on the charge generation layer. Thus, an electrophotographic photoconductor No. 1 according to the present invention was prepared.

EXAMPLES 2 TO 12

The procedure for preparing the electrophotographic photoconductor No. 1 in Example 1 was repeated except that Diane Blue serving as a charge generating material for use in the charge generation layer coating liquid and the tertiary amine Compound No. 6 serving as a charge transporting material for use in the charge transport layer coating liquid in Example 1 were respectively replaced by charge generating materials and charge transporting materials shown in the following Table 2, whereby electrophotographic photoconductors No. 2 to No. 12 according to the present invention were prepared.

TABLE 2
| Photoconductor No. | Charge Generating Material | Charge Transporting Material (Tertiary Amino Compound No.) |
|---|---|---|
| 1 | 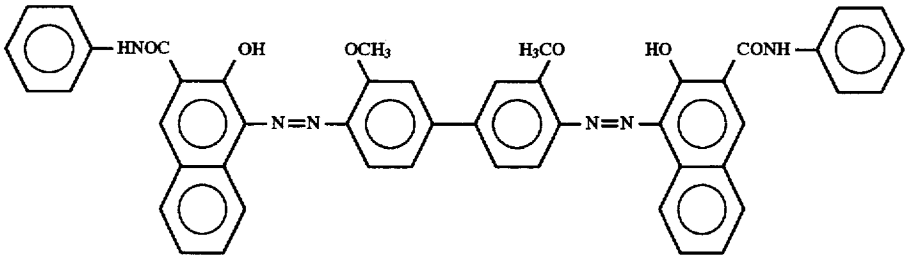 | 6 |
| 2 | 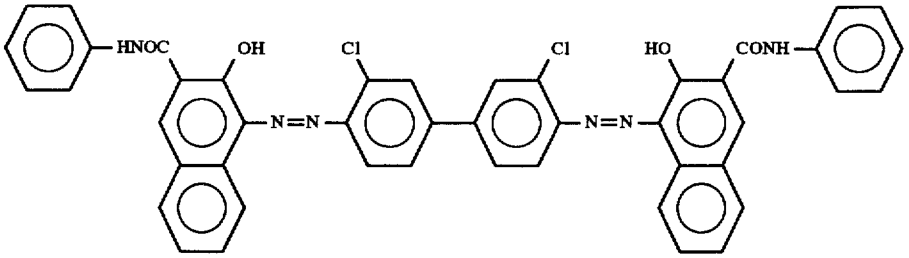 | 6 |
| 3 | 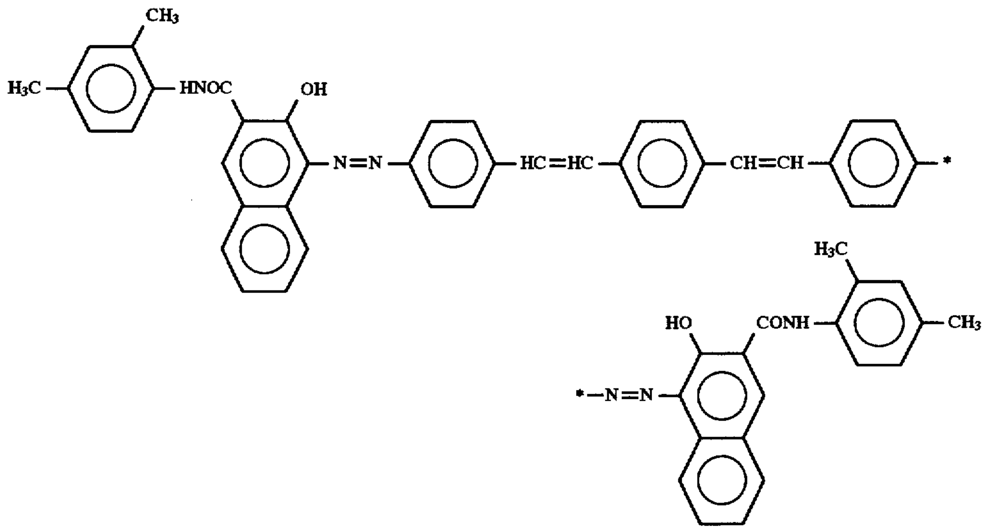 (herein referred to as P-1) | 6 |
| 4 | 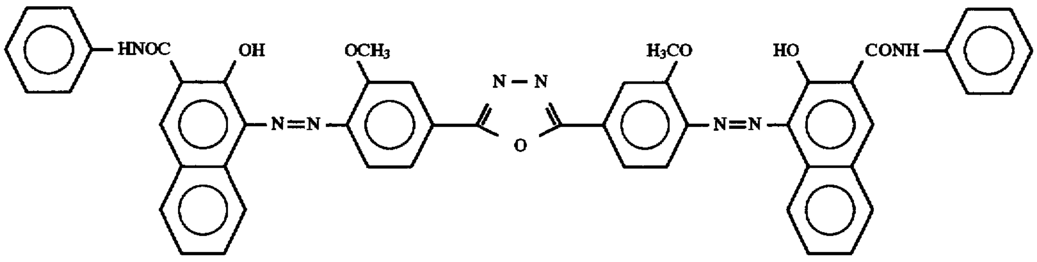 | 6 |

TABLE 2-continued
| Photoconductor No. | Charge Generating Material | Charge Transporting Material (Tertiary Amino Compound No.) |
|---|---|---|
| 5 | 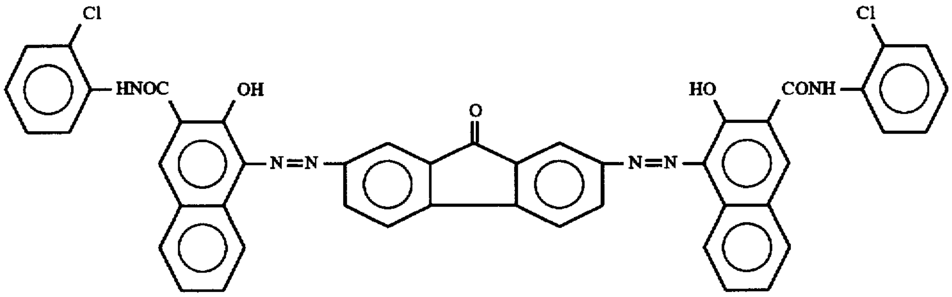 (hereinafter referred to as P-2) | 6 |
| 6 | 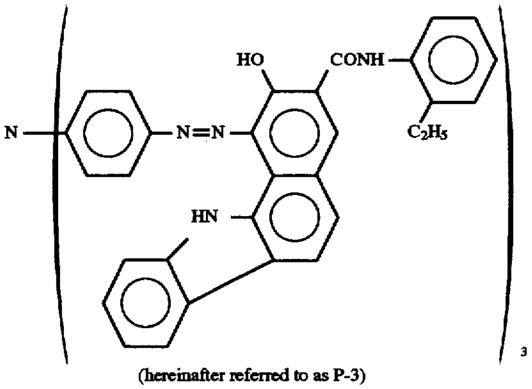 (hereinafter referred to as P-3) | 6 |
| 7 | β-type Copper Phthalocyanine | 6 |
| 8 | 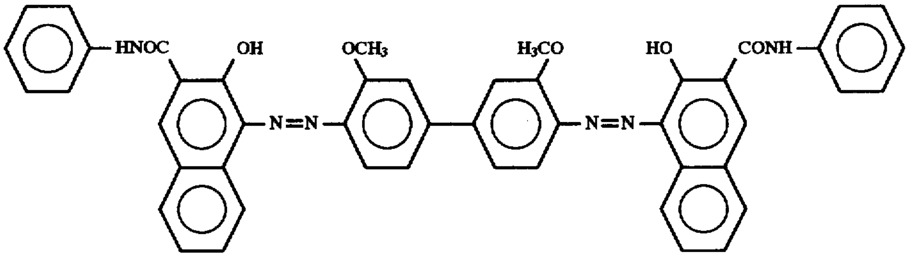 | 3 |
| 9 | 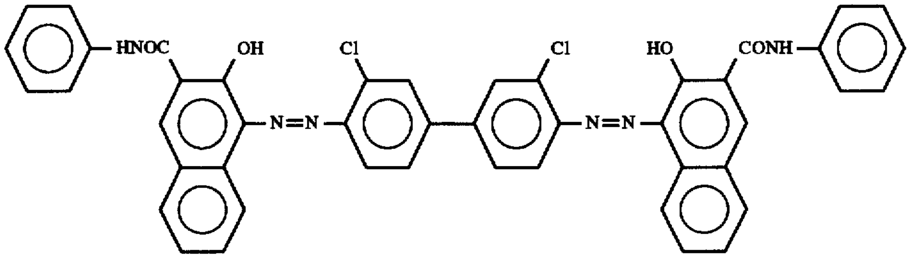 | 3 |
| 10 | P-1 | 3 |
| 11 | P-2 | 3 |
| 12 | P-3 | 3 |

EXAMPLE 13

7.5 parts by weight of a bisazo compound (P-2) serving as a charge generating material, and 500 parts by weight of 0.5% tetrahydrofuran solution of a polyester resin (Trademark "Vylon 200" made by Toyobo Company, Ltd.) were dispersed and ground in a ball mill.

The thus prepared dispersion was coated on an aluminum surface of an aluminum-deposited polyester film serving as an electroconductive substrate by a doctor blade, and dried at room temperature, so that a charge generation layer with a thickness of about 1 μm was formed on the electroconductive substrate.

One part by weight of the tertiary amine compound of the following formula (tertiary amine compound No. 3) serving as a charge transporting material, which was synthesized in Synthesis Example 3, was dissolved in a resin solution of 1 part by weight of polycarbonate resin (Trademark "Panlite K-1300" made by Teijin Chemicals Ltd.) and 8 parts by weight of tetrahydrofuran to prepare a coating liquid for a charge transport layer:

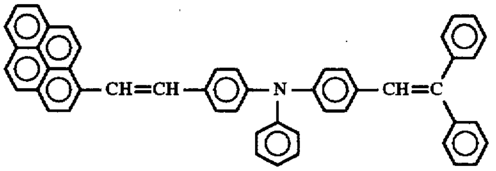

This liquid was coated on the above formed charge generation layer by a doctor blade, and dried at 80° C. for 2 minutes and then at 120° C. for 5 minutes, so that a charge transport layer with a thickness of about 20 μm was formed on the charge generation layer. Thus, an electrophotographic photoconductor No. 13 according to the present invention was prepared.

Comparative Example 1

The procedure for preparation of the electrophotographic photoconductor No. 13 in Example 13 was repeated except that the tertiary amine compound (compound No. 3) used as the charge transporting material in the charge transport layer coating liquid in Example 13 was replaced by a charge transporting material of the following formula:

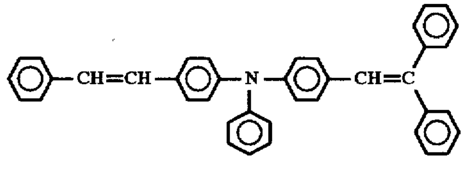

Thus, a comparative electrophotographic photoconductor No. 1 was prepared.

Each of the thus prepared electrophotographic photoconductors No. 1 to 13 according to the present invention and comparative electrophotographic photoconductor No. 1 was charged under application of −6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. Each photoconductor was then illuminated by a tungsten lamp in such a manner that the illuminance on the illuminated surface of the photoconductor was 4.5 lux, and the exposure $E_{1/2}$ (lux·sec) required to reduce the initial surface potential Vpo (V) to ½ thereof was measured. The results are shown in Table 3.

Furthermore, each of the electrophotographic photoconductors No. 1 to No. 12 according to the present invention was charged by use of a commercially available electrophotographic copying machine. Then, latent electrostatic images were formed on the photoconductor by subjecting the charged photoconductor to light exposure via an original. The thus formed latent electrostatic images were developed into visible images by a dry-type developer. The thus obtained toner images were electrostatically transferred to a sheet of plain paper and fixed thereon. As a result, clear images were transferred in any case. Clear images were also obtained when a wet-type developer was employed for development of the latent electrostatic images.

TABLE 3

| Example No. | $-V_{po}$ (V) | $E_{1/2}$ (lux · sec) |
|---|---|---|
| Ex. 1 | 1140 | 1.72 |
| Ex. 2 | 972 | 1.53 |
| Ex. 3 | 1210 | 0.98 |
| Ex. 4 | 1340 | 1.60 |
| Ex. 5 | 1086 | 0.83 |
| Ex. 6 | 690 | 0.40 |
| Ex. 7 | 1313 | 0.92 |
| Ex. 8 | 1010 | 1.30 |
| Ex. 9 | 930 | 1.02 |
| Ex. 10 | 730 | 0.62 |
| Ex. 11 | 956 | 0.96 |
| Ex. 12 | 720 | 0.43 |
| Ex. 13 | 956 | 0.96 |
| Comp. Ex. 1 | 569 | 1.16 |

The electrophotographic photoconductors of the present invention exhibit excellent chargeability and high photosensitivity. Furthermore, the photoconductors according to the present invention can be manufactured at low cost.

The triphenylamine compounds of formula (II) of the present invention effectively function as photoconductive materials in the electrophotographic photoconductors. Such triphenylamine compounds are optically or chemically sensitized with a sensitizer such as a dye or a Lewis acid, so that these compound are preferably employed as charged transporting materials in a photoconductive layer of the electrophotographic photoconductor, specifically of a function-separating type electrophotographic photoconductor comprising a charge generation layer and a charge transport layer.

Japanese Patent Application No. 6-247262 filed Sep. 14, 1994, Japanese Patent Application No. 6-247261 filed Sep. 14, 1994, Japanese Patent Application filed Sep. 11, 1995, and Japanese Patent Application filed Sep. 11, 1995 are hereby incorporated by reference.

What is claimed is:

1. A triphenylamine compound of formula (II):

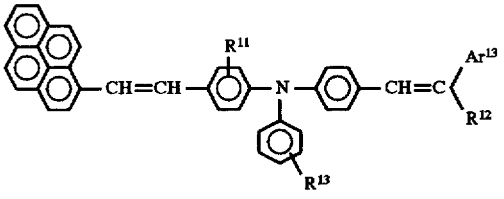

(II)

wherein $Ar^{13}$ is an aryl group which may have a substituent; $R^{11}$ and $R^{13}$ each is a hydrogen atom, an alkyl group or an alkoxy group; and $R^{12}$ is a hydrogen atom, an alkyl group which may have a substituent, or an aryl group which may have a substituent.

2. The triphenyl amine compound as claimed in claim 1, wherein the aryl group represented by $Ar^{13}$ is selected from the group consisting of phenyl group, naphthyl group, and biphenylyl group, which may be substituted with an alkyl group having 1 to 4 carbon atoms or with an alkoxyl group having 1 to 4 carbon atoms.

3. The triphenyl amine compound as claimed in claim 1, wherein the alkyl group represented by $R^{11}$ or $R^{13}$ is an alkyl group having 1 to 4 carbon atoms.

4. The triphenyl amine compound as claimed in claim 1, wherein the alkoxy group represented by $R^{11}$ or $R^{13}$ is an alkoxy group having 1 to 4 carbon atoms.

5. The triphenyl amine compound as claimed in claim 1, wherein the alkyl group represented by $R^{12}$ is an alkyl group having 1 to 4 carbon atoms, which may be substituted with an alkoxy group having 1 to 4 carbon atoms.

6. The triphenyl amine compound as claimed in claim 1, wherein the aryl group represented by $R^{12}$ is selected from the group consisting of phenyl group, naphthyl group, and biphenylyl group, which may be substituted with an alkyl group having 1 to 4 carbon atoms or with an alkoxy group having 1 to 4 carbon atoms.

* * * * *

UNITED STATES PATENT AND TRADEMARK OFFICE

CERTIFICATE OF CORRECTION

PATENT NO. : 5,672,756

DATED : September 30, 1997

INVENTOR(S) : Tomoyuki SHIMADA ET AL

It is certified that error appears in the above-identified patent and that said Letters Patent is hereby corrected as shown below:

In the title page, item [57], ABSTRACT, delete the Abstract in its entirety and replace with --An electrophotographic photoconductor includes an electroconductive substrate, and a photoconductive layer formed thereon containing at least one tertiary amine compound of formula (I) as an effective component:

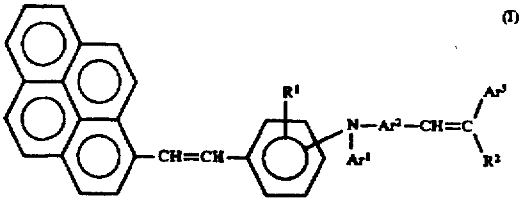

(I)

wherein $Ar^1$ and $Ar^3$ each is an aryl group which may have a substituent; $Ar^2$ is a bivalent group of a carbocyclic aromatic compound or a bivalent group of a heterocyclic compound; $R^1$ is a hydrogen atom, an alkyl group which may have a substituent or an alkoxy group which may have a substituent; and $R^2$ is a hydrogen atom, an alkyl group which may have a substituent or an aryl group which may have a substituent. A novel triphenylamine compound for use in the electrophotographic photoconductor is provided.--

UNITED STATES PATENT AND TRADEMARK OFFICE

CERTIFICATE OF CORRECTION

PATENT NO. : 5,672,756

DATED : September 30, 1997

INVENTOR(S) : Tomoyuki SHIMADA ET AL

It is certified that error appears in the above-identified patent and that said Letters Patent is hereby corrected as shown below:

Column 1, line 46, "manufacturability" should read --manufacturing--.

Column 2, line 18, "Publication" should read --Application--.

line 63, "carboxylic" should read --carbocyclic--.

Column 5, line 1, "$Ar^2$" should read --$R^2$--.

Column 13, line 24, "60-94967" should read --60-94978--.

line 27, "similarly, the" should read --similarly, and--.

line 50, "reaction by" should read --reaction be--.

Column 16, line 38, "preferably" should read --preferable--.

line 55, "C.I. Pigment Red (C.I. 21200) should read --C.I. Pigment Red 41(C.I. 21200)--.

line 62, "dibenzothiphene" should read --dibenzothiophene--.

UNITED STATES PATENT AND TRADEMARK OFFICE

CERTIFICATE OF CORRECTION

PATENT NO. : 5,672,756
DATED : September 30, 1997
INVENTOR(S) : Tomoyuki SHIMADA ET AL It is certified that error appears in the above-identified patent and that said Letters Patent is hereby corrected as shown below:

Column 17, line 1, "54-1773" should read --54-17733--.

line 15, "deposited deposited" should read --deposited--.

line 23, "adjusting" should read--adjustment--.

line 24, "layer 6" should read --layer 5--.

line 33, "preferably" should read --preferable--.

line 37, "5" should read --3--.

line 38, "preferably" should read --preferable--.

line 40, "generation layer 5 to be" should read --generation layer 5 be--.

Column 19, line 39, "20.10°C" should read --201.0°C--.

line 63, "4-formyl-4′(β-" should read --4-formyl-4′-(β---.

UNITED STATES PATENT AND TRADEMARK OFFICE
CERTIFICATE OF CORRECTION

PATENT NO. : 5,672,756

DATED : September 30, 1997

INVENTOR(S) : Tomoyuki SHIMADA ET AL

It is certified that error appears in the above-identified patent and that said Letters Patent is hereby corrected as shown below:

Columns 21-22, TABLE 2, between structures 3 and 4, "(herein referred to as P-1)" should read --(hereinafter referred to as P-1)--.

Column 22, TABLE 2, In the header, "Charge Transporting Material (Tertiary Amino Compound No.)" should read --Charge Transporting Material (Tertiary Amine Compound No.)--.

Column 24, TABLE 2-continued, "Charge Transporting Material (Tertiary Amino Compound No.)" should read --Charge Transporting Material (Tertiary Amine Compound No.)--.

Signed and Sealed this

Fourth Day of August, 1998

Attest:

Bruce Lehman

BRUCE LEHMAN

*Attesting Officer* *Commissioner of Patents and Trademarks*